(12) United States Patent
Clough

(10) Patent No.: US 6,938,363 B1
(45) Date of Patent: *Sep. 6, 2005

(54) ORTHOPEDIC SHOE APPLIANCE AND METHOD

(75) Inventor: James G. Clough, Great Falls, MT (US)

(73) Assignee: Cluffy Biomedical, LLC., Great Falls, MT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/693,235

(22) Filed: Oct. 20, 2000

Related U.S. Application Data

(63) Continuation-in-part of application No. 09/467,973, filed on Dec. 21, 1999, now Pat. No. 6,170,176.

(51) Int. Cl.⁷ ........................... A61F 5/14; A43B 13/12
(52) U.S. Cl. ..................... 36/140; 36/71; 36/81; 36/88; 36/117.5; 36/144; 36/166
(58) Field of Search ............................ 36/140, 71, 81, 36/88, 117.5, 142, 143, 144, 159, 155, 172, 36/28, 180, 166

(56) References Cited

U.S. PATENT DOCUMENTS

| | | | | |
|---|---|---|---|---|
| 1,847,973 A | * | 3/1932 | Morton | 36/180 |
| 2,616,190 A | * | 11/1952 | Darby | 36/144 |
| 2,990,629 A | * | 7/1961 | McLaughlin | 36/173 |
| 4,263,902 A | | 4/1981 | Dieterich | 128/81 R |
| 4,333,472 A | * | 6/1982 | Tager | 36/140 |
| 4,408,402 A | * | 10/1983 | Looney | 36/43 |
| 4,414,964 A | | 11/1983 | Farino et al. | 128/81 R |
| 4,745,927 A | * | 5/1988 | Brock | 36/140 |
| 4,852,553 A | | 8/1989 | Voykin | 128/25 B |
| 4,940,046 A | * | 7/1990 | Jacoby | 602/30 |
| 5,327,663 A | * | 7/1994 | Pryce | 36/144 |
| 5,694,705 A | | 12/1997 | Alonso Coves | 36/44 |
| 5,881,478 A | * | 3/1999 | McMahon et al. | 36/144 |
| 6,092,314 A | * | 7/2000 | Rothbart | 36/144 |
| 6,098,319 A | * | 8/2000 | Epstein | 36/159 |
| 6,170,176 B1 | * | 1/2001 | Clough | 36/140 |
| 6,182,380 B1 | * | 2/2001 | Liley | 36/71 |
| 6,212,723 B1 | * | 4/2001 | Rothbart | 12/133 R |

* cited by examiner

Primary Examiner—Jila M. Mohandesi
(74) Attorney, Agent, or Firm—Osha Liang L.L.P.

(57) ABSTRACT

An apparatus for orthopedic treatment including a top surface, a bottom surface, and an angle of inclination formed between the top surface and the bottom surface is disclosed. In addition, the apparatus, in some embodiments, may be integrally formed as part of a piece of footwear. A method for providing stability during ambulation including providing and insert and elevating a toe using the insert is also disclosed. Also disclosed is an apparatus for orthopedic treatment wherein the angle of inclination is between approximately 1 and 60 degrees. Also disclosed is an apparatus for orthopedic treatment manufactured from an elastomeric material. Also disclosed is an apparatus for orthopedic treatment, where the top surface further includes at least one fastener.

23 Claims, 8 Drawing Sheets

Figure 3
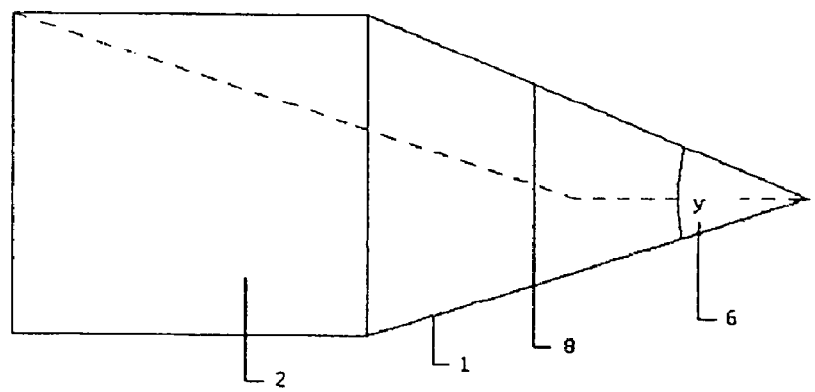
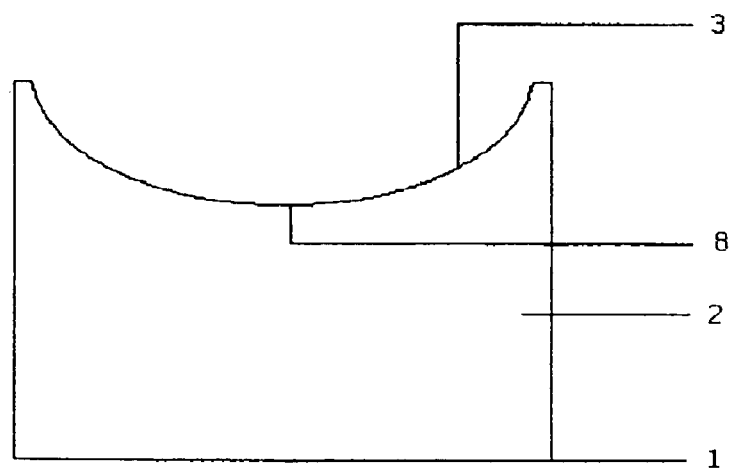
Figure 4

ORTHOPEDIC SHOE APPLIANCE AND METHOD

CROSS REFERENCE TO RELATED APPLICATIONS

This application is a continuation-in-part of U.S. patent application Ser. No. 09/467,973, filed Dec. 21, 1999 now U.S. Pat. No. 6,170,176.

BACKGROUND

DESCRIPTION OF RELATED ART

When a person ambulates, or moves from place to place such as by walking, a host of triplane motions occur to the foot structure, broadly termed pronation and supination. Pronation generally involves rotation of a joint or part in a forward direction or toward the midline of the body. Supination generally involves rotation of a joint or part in an outward direction or away from the midline of the body. When a person over-pronates, or for any other reason places too much force on the inside of the foot, excessive mobility of the medial arch area of the foot can result. The resulting foot instability can be manifested as arch, foot, ankle, and/or leg pain, as well as postural problems from excessive internal rotation of the leg.

Conventional orthopedic corrective devices described to address this problem include many different types. However, none provide for an orthopedic shoe appliance specifically adapted to provide improved stability of the foot structure, and a method of providing for improved stability of the foot structure, during ambulation in the manner which is provided for in the present invention.

U.S. Pat. No. 5,881,478, issued Mar. 16, 1999 to McMahon et al. teaches a shoe having a resilient sole, an upper secured to the sole, and a rockable member within a cavity in the sole. The rockable member being configured for side-to-side rocking in the sole cavity between a neutral position and a tilted position as the wearer's foot is moved relative to the sole between a neutral position as the wearer's foot is moved relative to the sole between a neutral position and a tilted position.

U.S. Pat. No. 5,694,705, issued Dec. 9, 1997 to Alonso Coves teaches an insole formed by the combination of two laminar bodies, one of split leather and the other of rubber material being provided with knobs forming support projections for the foot.

U.S. Pat. No. 4,852,553, issued Aug. 1, 1989 to Voykin teaches a foot zone reflex self-administering therapy apparatus comprising a display board adapted to display foot reflexology zones corresponding to anatomical areas of the body and stimulating members adapted to be placed on the display board at a zone corresponding to an anatomical area of the body requiring therapy.

U.S. Pat. No. 4,414,964, issued Nov. 15, 1983 to Farino et al. teaches a post-operative pliable protector device for the hallux or big toe having a cushion pad with at least a portion thereof adapted to encircle the toe and being formed with a separable fastener having a loop-type fabric.

U.S. Pat. No. 4,408,402 issued Oct. 11, 1983 to Looney teaches a supportive shoe or insert which provides increased support to specific areas of the foot during the first, second and third trimesters of pregnancy to compensate for changes in body weight and center of gravity. A pad, which can be a shoe insole, is provided with these specific areas of support.

U.S. Pat. No. 4,333,472, issued Jun. 8, 1982 to Tager teaches compensatory-corrective orthopedic foot devices comprising of the construction and specific application of a series of differentially-sized geometrically-shaped and specifically configured, generally wedge-shaped, prosthetic devices that are utilized in the compensatory treatment of specific clinical structural biomechanical abnormalities of the human foot.

U.S. Pat. No. 4,263,902, issued Apr. 28, 1981 to Dietrich teaches an orthopedic sandal for correction of hammer-toes and X-toe comprising a dual lever arm arrangement pivotable on a horizontal axis transverse to the sole. Additionally, a pressure element for pressing the toes downward in on one arm and the other arm is fastened to the rearward portion of the foot so that as the foot is lifted, the pressure element is pressed downwardly on the hammer-toes.

None of the art as identified above, either individually or in combination, describes an orthopedic appliance nor a method, which specifically provides for improved stability of the foot structure during ambulation. Many individuals suffer from a functional limitation of the hallux, (big toe), motion with ensuing joint pathology and pain. Additionally, many people suffer from abnormal weight distribution on the ball of the foot with lesser metatarsalgia complaints. Over-pronation can be a contributing factor to a host of other foot ailments as well as contributing to abnormal mechanics of the ankle, knee, hip and lower back. This problem is common and has been a topic of concern by shoe manufacturers and podiatrists attempting to achieve foot comfort. However, the prior art has not accomplished improving both stability and comfort during ambulation.

SUMMARY OF THE INVENTION

The invention relates to a method and apparatus for improving stability of the foot structure during ambulation. In one aspect, the invention relates to an orthopedic apparatus comprising a top surface, a bottom surface, and an angle of inclination formed between the top surface and the bottom surface.

In another aspect, the invention relates to an orthopedic apparatus that is integrally formed as part of a piece of footwear.

In another aspect, the invention relates to an orthopedic apparatus comprising a top surface, a bottom surface, and a means for supporting a toe at an angle of inclination.

In another aspect, the invention relates to a method of improving stability during ambulation comprising providing an insert, and elevating a toe to a predetermined angle of inclination.

BRIEF DESCRIPTION OF THE DRAWINGS

FIG. 3 is a perspective view of one embodiment of the present invention.

FIG. 4 is an end view of one embodiment of the present invention.

DETAILED DESCRIPTION OF INVENTION

Figure 1:
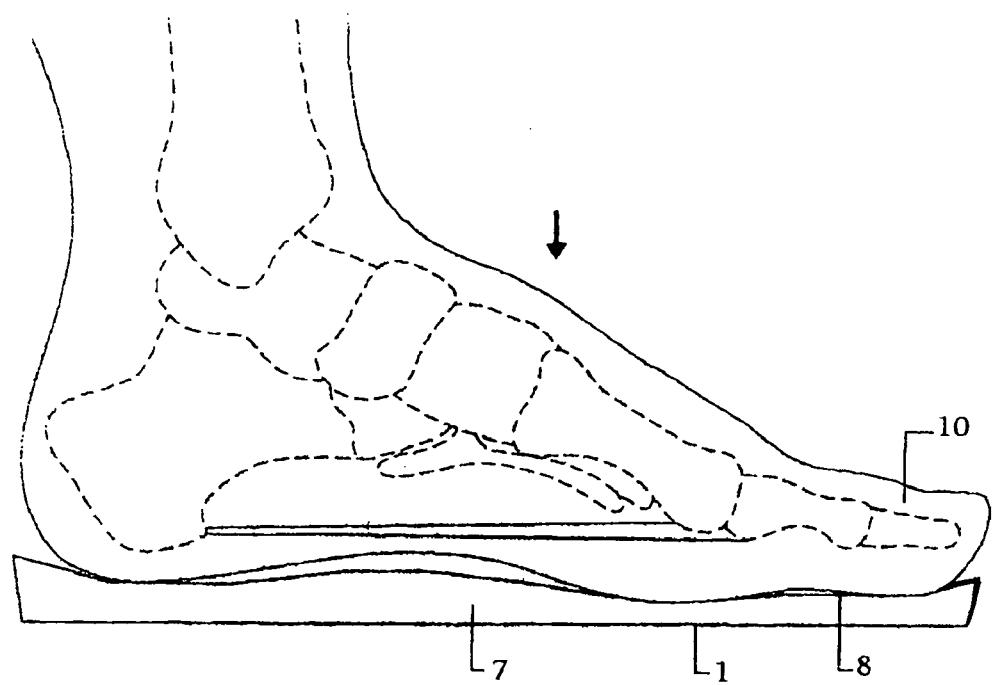
FIG. 1 is a prior art figure illustrating the bone structure of a foot on a typical piece of footwear.

First, this invention improves the stability of the foot structure during ambulation. With increased medial column stability of the foot, pain is alleviated in the lesser metatarsal area of the foot. Elevation of the hallux accomplishes several significant biomechanical sequences which have the effect of providing a supinatory position of the subtalar and midtarsal joints as well as pronation of the longitudinal midtarsal joint. As dorsiflexion of the toes takes place in late midstance and early propulsion, the plantar fascia is placed on stretch. As this occurs, the arch height is increased or the distance between the heel and the ball of the foot is shortened. This results in overall supination of the foot structure which provides for more stability of the foot during stance.

The second advantage to the present invention is alleviation of foot pain caused by limited dorsiflexion of the first metatarsalphlangeal joint. A pronated rearfoot and a supinated forefoot (a flat foot) places the aponeurosis (plantar fascia) under stress. Stress without dorsiflexion of the metatarsalphlangeal joints will result in marked limitation of dorsiflexion of the first metatarsalphlangeal joint causing pain. Use of the present invention prestresses the plantar fascia without limiting the motion of the metatarsalphlangeal joint, alleviating pain caused by stress without dorsiflexion.

The third advantage of the present invention is that it allows for rotation of the hallux around the first metatarsal decreasing the likelihood of degenerative conditions arising over time such as structural hallux rigidus. In normal gait, the first metatarsal hits the surface maximally dorsiflexed. After relaxation of the anterior tibial muscle, the first metatarsal should move towards the weight bearing surface (plantarflex). This is facilitated by rearfoot supination. This plantarflexion is essential for the first metatarsalphlangeal joint to dorsiflex normally in propulsion. The first metatarsalphlangeal joint (big toe joint) must dorsiflex before plantarflexion of the first metatarsal takes place. By placing the hallux in a dorsiflexed position, as this invention does, the first metatarsal is plantarflexed such that excessive dorsiflexion of the first metatarsal cannot occur with weight bearing reactive forces. The net effect of this is to pronate the longitudinal midtarsal joint axis.

In an abnormal gait without proper foot function, the metatarsal elevates and the first metatarsalphlangeal joint axis is also elevated. Such elevation limits the ability of the hallux to rotate around the elevated first metatarsal segment and is termed functional hallux limitus. When functional hallux limitus occurs over a prolonged period of time, a degenerative joint disease called hallux rigidus may develop. Elevation of the first metatarsal can occur whenever a person over-pronates or bears too much weight through the medial (inside) column of the foot. Over pronation is a common biomechanical error in terminal stance and shoe designers for years have been attempting to control abnormal degrees of this motion. However, by using the present invention, the motion of the hallux is improved in the user, limiting further development of functional hallux limitus and hallux rigidus.

The fourth advantage of this invention is ease of application. The invention may be disposed beneath the hallux in various ways, including formation as part of the sole of footwear, adhesion of the wedge to the inner sole of footwear after manufacture, and adhering the wedge to the hallux for use in the absence of footwear. While manufacture of the present invention can be accomplished in a large scale production, the present invention may also be manufactured in a doctor's office such that they may be custom fit to the individual wearer.

FIG. 1 shows a typical view of the foot at rest on a typical shoe insole 7. The hallux 10 is resting on an upper planar surface 8 of the insole 7 that is parallel to a lower planar surface 1 of the insole 7. Without supporting the hallux 10, there is increased likelihood that there will be excessive mobility of the medial arch area of the foot.

Figure 2:
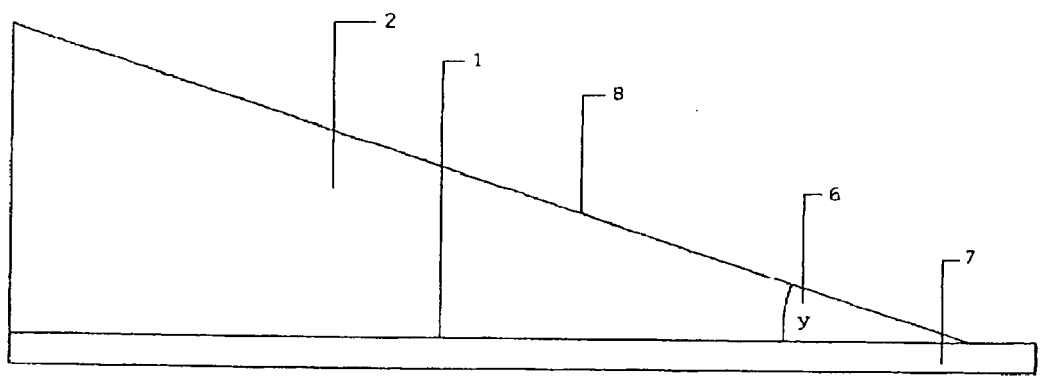
FIG. 2 is a side view of one embodiment of the present invention.

FIG. 2 shows a typical embodiment of the present invention. While the description of the following embodiments recites specific structures such as a wedge, any similar structure may be used, and the scope of the invention should not be limited in any way except by the attached claims. The orthopedic apparatus comprises a wedge 2 that has an upper planar surface 8, upon which the hallux rests, that is separated from a lower planar surface 1 by an angle y 6. The angle y 6 is preferably in a range approximately between 1 to 60 degrees for normal ambulation. The angle y 6 can be either increased or decreased depending on the amount of correction desired and the heel height of the shoe. Increased footwear heel height places the hallux at an increased angle of flexion, thus reducing the angle y needed for proper stability. The wedge 2 may be made of any suitable material commonly employed for such purposes such as flexible material, leather, resilient foam-like material, cork, thermoplastic, or various combinations of materials. The wedge 2 provides a means to elevate the hallux up from the insole 7 and thus up from the floor. The overall length and width of the wedge 2 can vary dependant on the individual hallux to be elevated. The wedge 2 will function to stabilize the first metatarsal against ground reactive forces and limit displacement of the first metatarsal upward. Thus, the first metatarsal will plantarflex more easily through the late midstance and propulsive phases of gait. By placing the plantar aponeurosis on stretch there will result a retrograde effect at stabilizing the joints more proximally referred to as the midtarsal joint and the subtalar joint with improved joint congruity and alignment of the foot in relationship to the leg during ambulation. When the first metatarsalphlangeal joint is able to dorsiflex, normal plantarflexion of the first metatarsal is possible and the normal mechanics of the gait cycle are not disrupted during ambulation. The wedge 2 provides for such dorsiflexion of the first metatarsalphlangeal joint of the foot.

In this embodiment, the wedge 2 may be adhered along the lower planar surface 1 to the planar surface of footwear where the hallux normally rests. The wedge 2 also may be adhered to the hallux along the upper planar surface 8.

FIG. 3 shows a perspective view of a typical embodiment of the orthopedic appliance where the wedge 2 includes the upper planar surface 8, the lower planar surface 1 and the angle y 6. In this embodiment, the wedge 2 may be adhered along the lower planer surface 1 to the planar surface of footwear where the hallux normally rests. The wedge 2 also may be adhered to the hallux along the upper planar surface 8. Adhering the wedge to the hallux along the upper planar surface 8, rather than to the planar surface of footwear where the hallux normally rests, allows the invention to be used in the absence of footwear.

FIG. 4 shows an end view of a typical embodiment of the orthopedic appliance. In this embodiment, the wedge 2 includes a concave depression 3 in the upper planar surface 8 running along the wedge 2 cradling the hallux. The concave depression 3 provides for disposing the hallux in the proper position along the upper planer surface 8.

Figure 5:
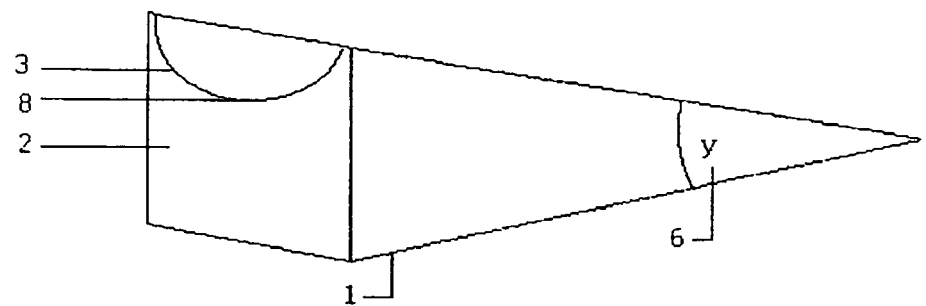
FIG. 5 is a perspective view of one embodiment of the present invention illustrating a concave depression in a top surface.

FIG. 5 shows a perspective view of the orthopedic appliance shown in FIG. 4.

Figure 6:
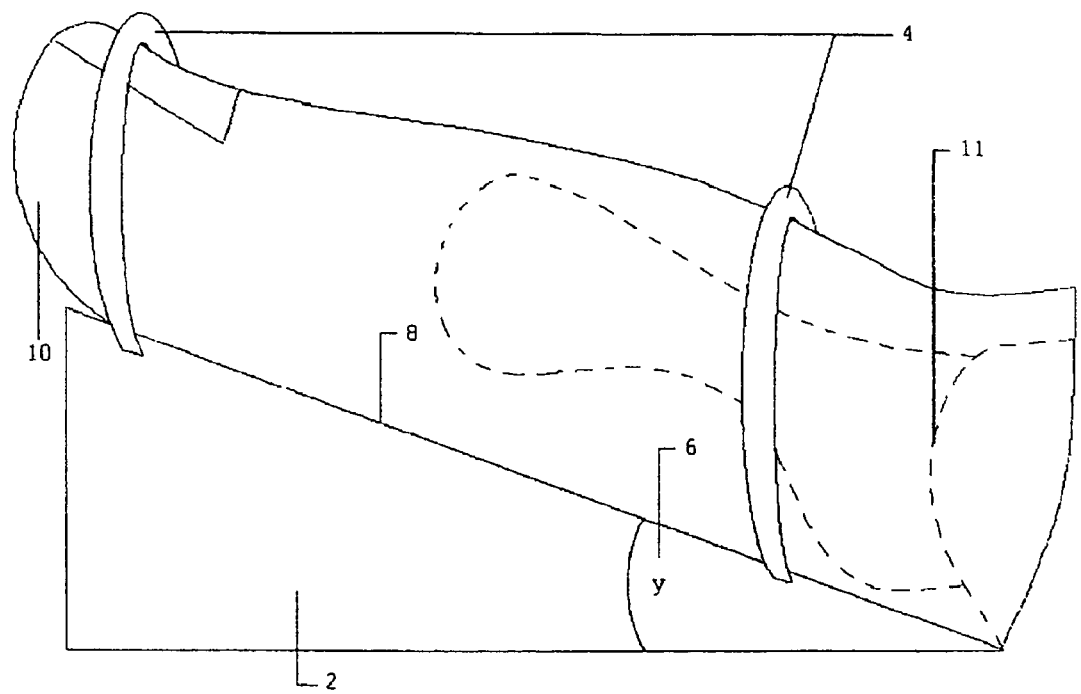
FIG. 6 is a side view of one embodiment of the present invention with fasteners.

FIG. 6 shows a side view of a typical embodiment of the orthopedic appliance. In this embodiment, the appliance is made up fasteners 4 disposed above the upper planar surface 8 of the wedge 2. The fasteners 4 provide for adhering the wedge 2 to the hallux 10. The hallux 10 is disposed between the fasteners 4 and the upper planar surface 8 in a manner such that the hallux rests at an increased angle y 6 from the metatarsalphlangeal joint 11 to the end of the hallux 10 along the upper planar surface 8 of the wedge 2. The fasteners 4 provide for proper disposition of the wedge 2 beneath the hallux 10 by keeping the hallux 10 in constant contact with the upper planar surface 8 of the wedge 2.

Figure 7:
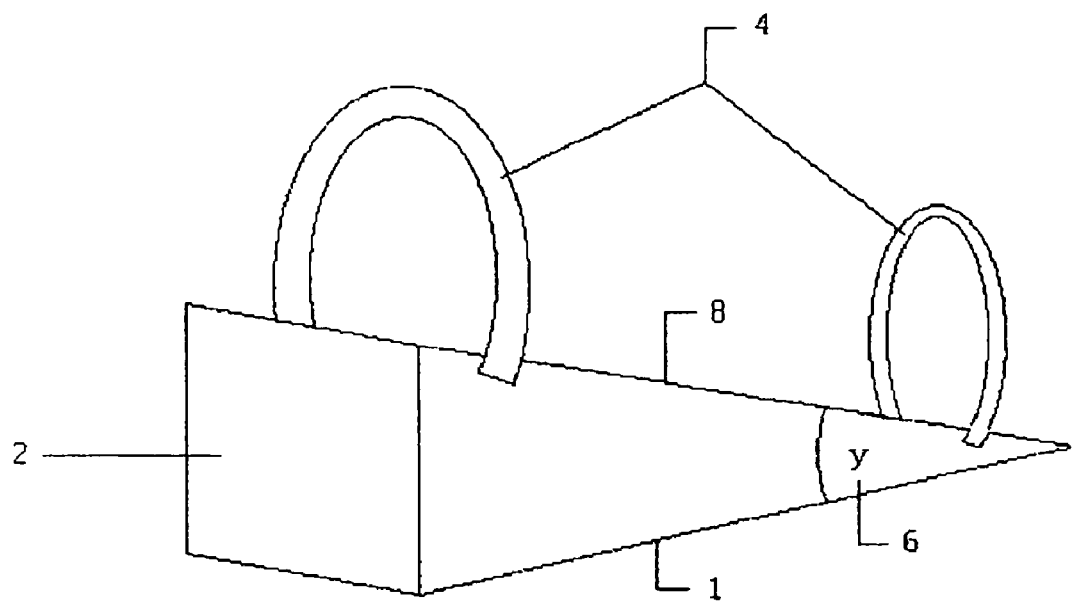
FIG. 7 is a perspective view of one embodiment of the present invention with fasteners.

FIG. 7 shows a perspective view of the orthopedic appliance as shown in FIG. 6.

Figure 8:
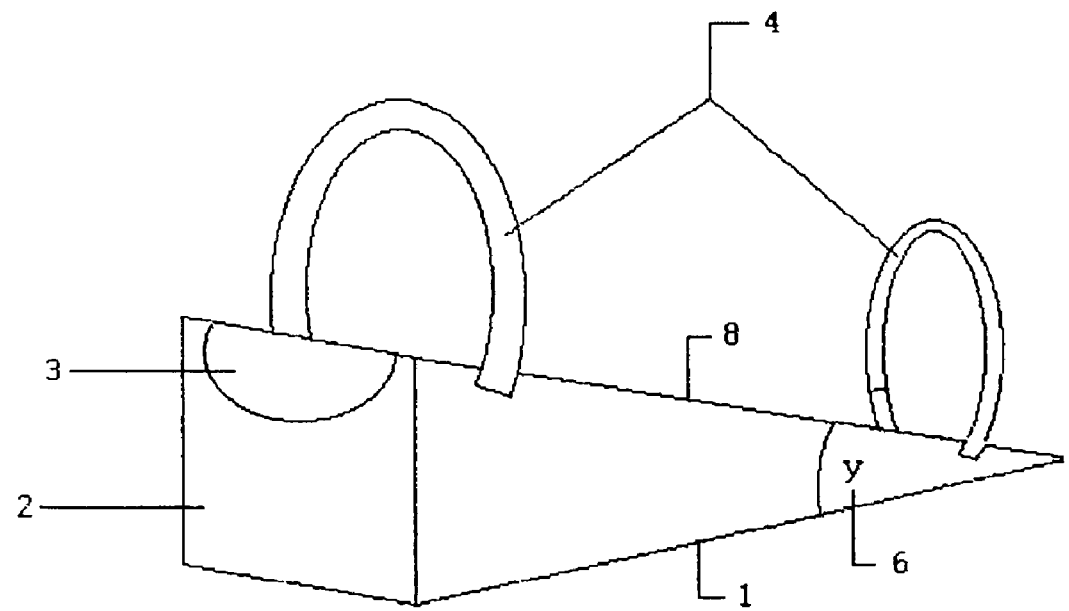
FIG. 8 is a perspective view of one embodiment of the present invention with fasteners and a concave depression.

FIG. 8 shows a perspective view of the orthopedic appliance shown in FIG. 6 with the addition of a concave depression 3 to the wedge 2. The concave depression 3 in the upper planar surface 8 running along the wedge 2 cradles the hallux. In addition to the fasteners 4, the concave depression 3 provides for disposing the hallux in the proper position along the upper planer surface 8.

Figure 9:
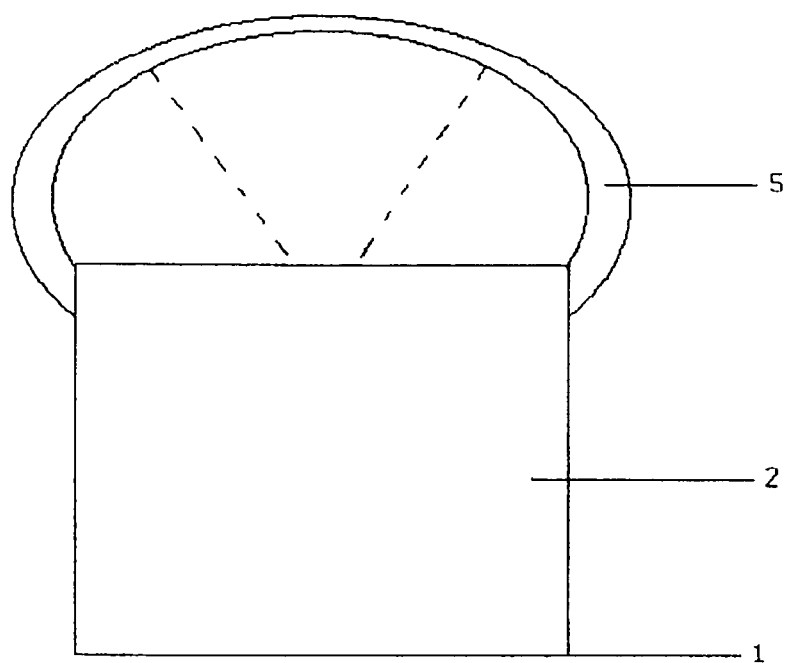
FIG. 9 is an end view of one embodiment of the present invention with a single hallux encompassing fastener.

FIG. 9 is an end view of one embodiment of the orthopedic appliance comprising a fastener 5 connected to the wedge 2 rather than a plurality of fasteners as shown in FIG. 6. The hallux is disposed between the fastener 5 and the upper planar surface 8 in a manner such that the hallux rests at an increased angle from the lower planar surface 1 of the wedge 2. The fastener 5 creates pressure along the length of the hallux adhering the wedge 2 and the hallux, providing for proper disposition of the wedge 2 beneath the hallux by keeping the hallux in constant contact with the upper planar surface 8.

Figure 10:
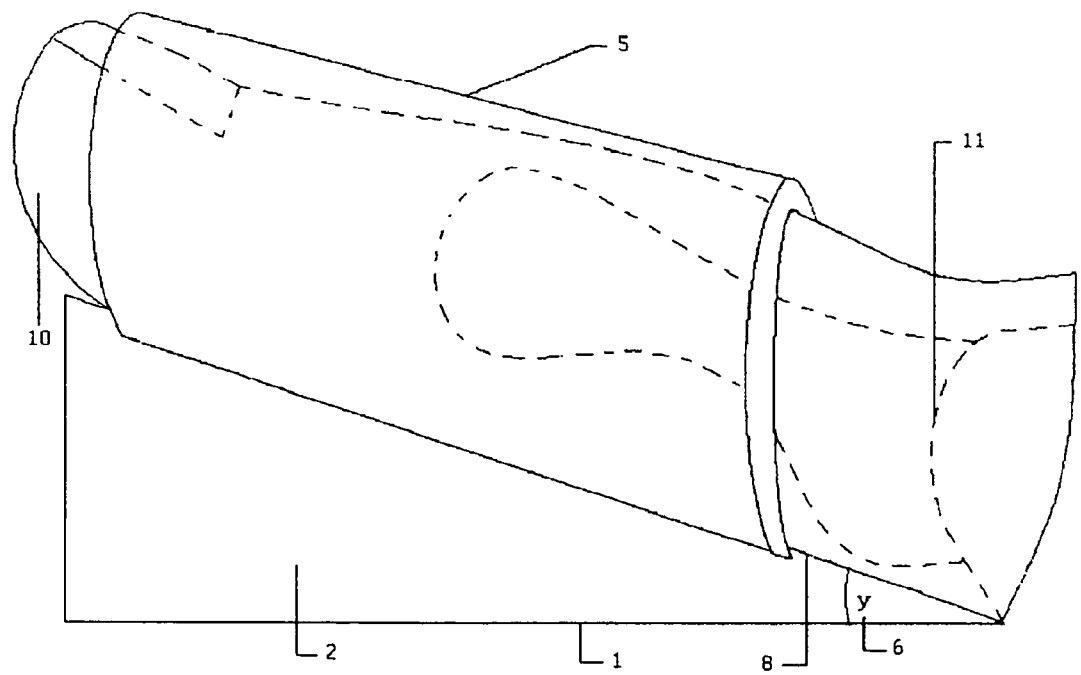
FIG. 10 is a side view of one embodiment of the present invention with a single hallux encompassing fastener.

FIG. 10 is a side view of the embodiment of the orthopedic appliance as shown in FIG. 9. In this embodiment, the appliance is made up a fastener 5 disposed above the upper planar surface 8 of the wedge 2. The fastener 5 provides for adhering the wedge 2 to the hallux 10. The hallux 10 is disposed between the fastener 5 and the upper planar surface 8 in a manner such that the hallux 10 rests at an increased angle y 6 from the metatarsalphlangeal joint 11 to the end of the hallux 10 along the upper planar surface 8 of the wedge 2. The fastener 5 provides for proper disposition of the wedge 2 beneath the hallux 10 by keeping the hallux 10 in constant contact with the upper planar surface 8.

Figure 11:
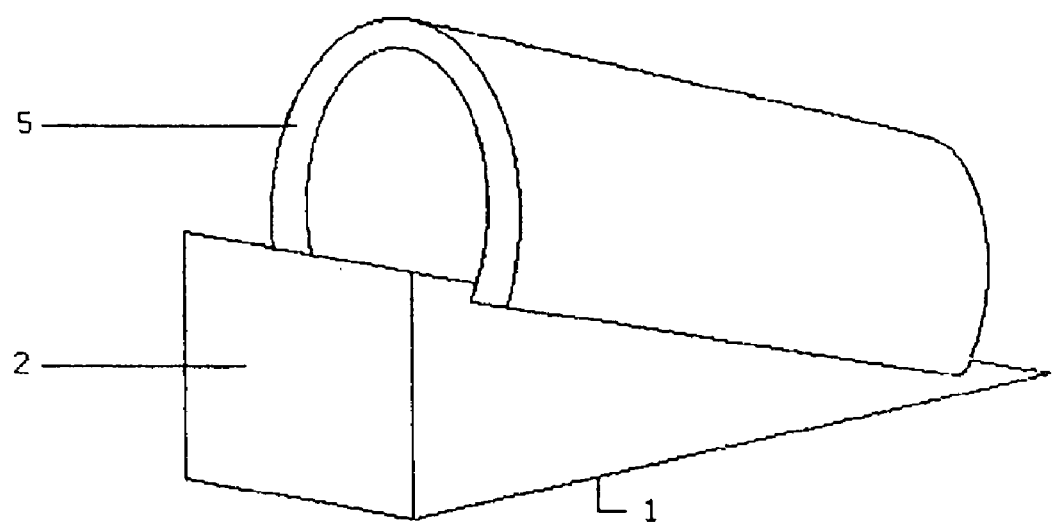
FIG. 11 is a perspective view of one embodiment of the present invention with a single hallux encompassing fastener.

FIG. 11 is perspective view of the embodiment of the orthopedic appliance as shown in FIG. 9.

Figure 12:
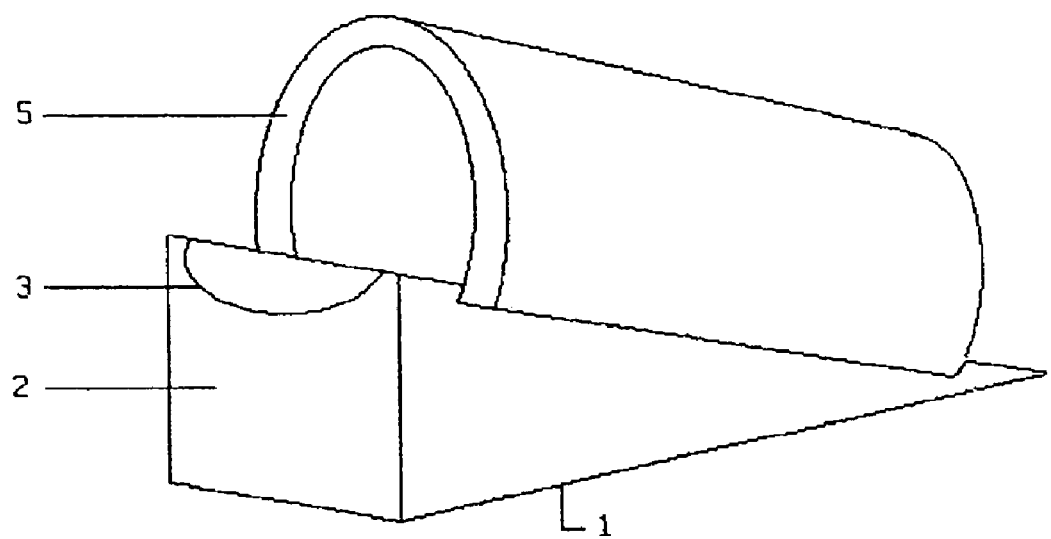
FIG. 12 is a perspective view of one embodiment of the present invention with a single hallux encompassing fastener and a concave depression.

FIG. 12 is a perspective view of an embodiment of the orthopedic appliance with the addition of a concave depression 3 to the wedge 2. The concave depression 3 in the upper planar surface 8 running along the wedge 2 cradles the hallux. In addition to the fastener 5, the concave depression 3 provides for disposing the hallux in the proper position along the upper planer surface 8.

Figure 13:
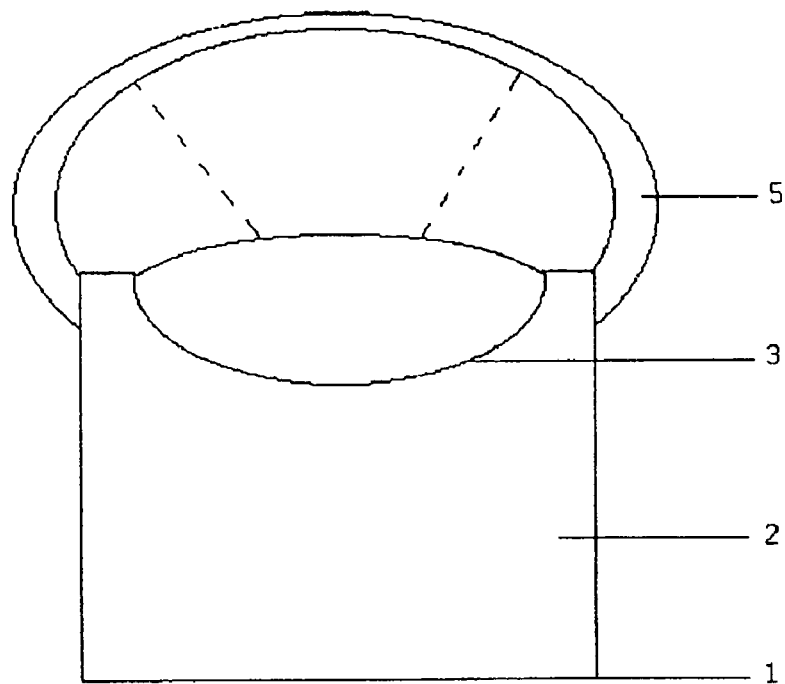
FIG. 13 is an end view of one embodiment of the present invention with a single hallux encompassing fastener and a concave depression.

FIG. 13 is an end view of the embodiment of the orthopedic appliance shown in FIG. 12.

Figure 14:
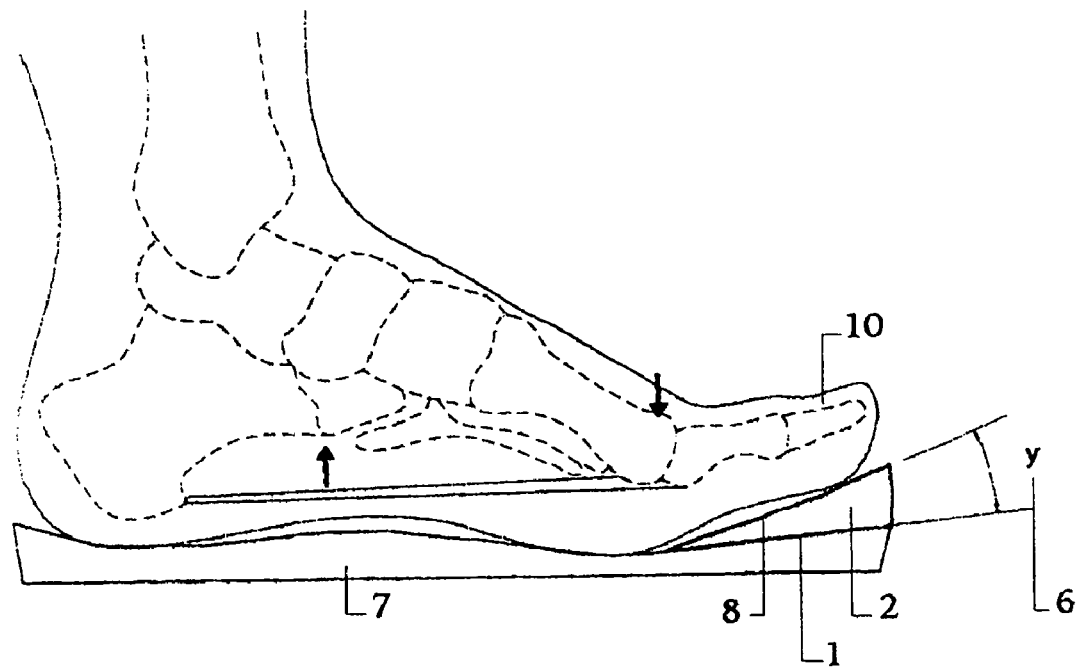
FIG. 14 is a perspective view of one embodiment of the present invention molded as a part of the sole of footwear.

FIG. 14 is a side view of the appliance shown in FIG. 1 where the wedge 2 has been adhered along the lower planar surface 1 of the wedge 2 to the insole 7 of footwear, or the wedge 2 has been molded as a single piece with the insole 7 of the footwear. The hallux 10 is disposed along the upper planar surface 8 at an angle y 6.

Figure 15:
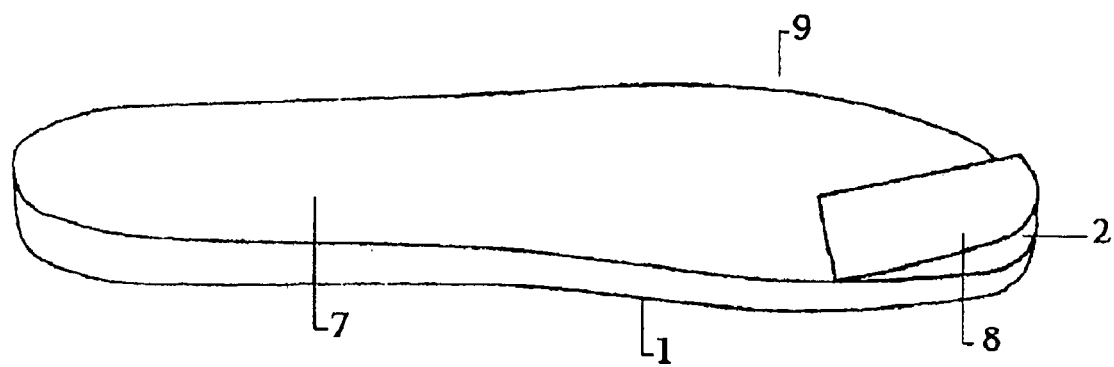
FIG. 15 is a side view of the bone structure of the foot illustrating one embodiment of the present invention elevating the hallux.

FIG. 15 shows a perspective view of the orthopedic appliance. The wedge 2 had been formed as part of the insole 7. However, the wedge might also be formed as part of the midsole, or exterior sole of the shoe.

While the invention has been described with respect to a limited number of embodiments, those skilled in the art will appreciate that other embodiments can be devised which do not depart from the scope of the invention as disclosed herein. Accordingly, the scope of the invention should be limited only by the attached claims.

What is claimed is:

1. An orthopedic appliance, comprising a wedge adapted to be placed under the phalanges of a toe and to not extend under the center of a first metatarsal, the wedge having a top surface adapted to support the toe and a bottom surface, wherein the wedge is inclined such that when properly sized and placed, an angle of inclination between the top surface and the bottom surface of the wedge deflects a proximal phalanx of the toe between 1 and 60 degrees upwardly in a first proximal phalanx to a first distal phalanx direction, relative to the first metatarsal.

2. The orthopedic appliance of claim 1, wherein the angle of inclination is between 10 and 20 degrees.

3. The orthopedic appliance of claim 1, wherein the wedge is formed integrally as part of a piece of footwear.

4. The orthopedic appliance of claim 1, wherein the wedge comprises an elastomeric material.

5. The orthopedic appliance of claim 1, wherein the wedge comprises a material selected from the group consisting of: cork, leather, resilient foam, and thermoplastic material.

6. The orthopedic appliance of claim 1, wherein a concave depression is formed in the top surface.

7. The orthopedic appliance of claim 1, further comprising at least one fastener.

8. The orthopedic appliance of claim 7, wherein the at least one fastener comprises a plurality of bands disposed adjacent the top surface.

9. The apparatus of claim 7, wherein the at least one fastener comprises a sheath disposed over the top surface.

10. An apparatus for orthopedic treatment, comprising:
   i. a top surface adapted to support the phalanges of a toe and not extending under the center of a first metatarsal;
   ii. a bottom surface; and
   iii. a support which, when the apparatus is properly sized and placed, deflects a proximal phalanx of the toe upwardly at an angle of inclination in a first proximal phalanx to a first distal phalanx direction between the top surface and the bottom surface.

11. The apparatus of claim 10, wherein the angle of inclination is between 1 and 60 degrees.

12. The apparatus of claim 10, wherein the angle of inclination is between 10 and 20 degrees.

13. The apparatus of claim 10, wherein the support is formed integrally as part of a piece of footwear.

14. The apparatus of claim 10, wherein a concave depression is formed in the top surface.

15. The apparatus of claim 10, further comprising at least one fastener.

16. The apparatus of claim 15, wherein the at least one fastener comprises a plurality of bands disposed adjacent the top surface.

17. The apparatus of claim 15, wherein the at least one fastener comprises a sheath disposed over the top surface.

18. A method for improving stability of a foot during ambulation, comprising:

i. providing a wedge having a top surface adapted to be positioned substantially under the phalanges of a toe and to not extend under the center of a first metatarsal, and a bottom surface; and ii. upwardly deflecting a proximal phalanx of the toe relative to the first metatarsal to a predetermined angle of inclination in a first proximal phalanx to a first distal phalanx direction using the wedge.

19. The method of claim 18, wherein the angle of inclination is between approximately 1 and 60 degrees.

20. The apparatus of claim 18, wherein the angle of inclination is between 10 and 20 degrees.

21. The method of claim 18, further comprising fixing the bottom surface of the wedge to a piece of footwear.

22. The method of claim 18, further comprising fixing the wedge to the toe using at least one band.

23. The method of claim 18, further comprising fixing the wedge to the toe using a sheath.

* * * * *